United States Patent [19]

Oda et al.

[11] Patent Number: 5,582,169

[45] Date of Patent: Dec. 10, 1996

[54] METHOD AND APPARATUS FOR MEASURING CONCENTRATION OF ABSORPTIVE CONSTITUENT IN SCATTERING MEDIUM

[75] Inventors: Motoki Oda; Yutaka Yamashita; Kazuyoshi Ohta, all of Hamamatsu; Mamoru Tamura; Goro Nishimura, both of Sapporo, all of Japan

[73] Assignee: Hamamatsu Photonics K.K., Hamamatsu, Japan

[21] Appl. No.: 257,039

[22] Filed: Jun. 8, 1994

[30] Foreign Application Priority Data

Jun. 10, 1993 [JP] Japan .................................. 5-138736

[51] Int. Cl.⁶ ......................................................... A61B 5/00
[52] U.S. Cl. ........................................... 128/633; 128/664
[58] Field of Search ................................... 128/633, 664; 356/39, 40, 41

[56] References Cited

U.S. PATENT DOCUMENTS

| | | |
|---|---|---|
| 4,857,748 | 8/1989 | Takiguchi . |
| 4,972,331 | 11/1990 | Chance . |
| 5,090,415 | 2/1992 | Yamshita et al. . |
| 5,119,815 | 6/1992 | Chance . |
| 5,386,827 | 2/1995 | Chance et al. ........................ 128/633 |
| 5,413,098 | 5/1995 | Benaron ............................... 128/633 |
| 5,805,623 | 2/1989 | Jobsis . |

FOREIGN PATENT DOCUMENTS

| | | |
|---|---|---|
| 0329115 | 8/1989 | European Pat. Off. . |
| 4192642 | 7/1992 | Japan . |
| 9009003 | 8/1990 | WIPO . |

OTHER PUBLICATIONS

Wilson et al, "Time–Dependent Optical Spectroscopy and Imaging for Biomedical Applications", Proceedings of the IEEE, vol. 80, No. 6, Jun. 1992, pp. 918–930.

Nomura et al, "Picosecond Time of Flight Measurement of Living Tissue: Time Resolved Beer–Lambert Law", Oxygen Transport of Tissue XIII, Plenum Press, New York, 1992, pp. 131–136.

Sevick et al, "Quantitation of Time– and Frequency–Resolved Optical Spectra for the Determination of Tissue Oxygenation", Optical Determination of Hemoglobin Saturation in Tissue, AP–Anal Bio, pp. 1–22.

Patterson et al, "Time Resolved Reflectance and Transmittance for the Non–Invasive Measurement of Tissue Optical Properties", Applied Optics, vol. 28, No. 12, Jun. 1989, pp. 2331–2335.

Delpy et al, "Estimation of Optical Pathlength Through Tissue From Direct Time of Flight Measurement", Phys. Med. Biol. 1988, vol. 33, No. 12, 1433–1442.

Jobsis, "Noninvasive, Infrared Monitoring of Cerebral and Myocardial Oxygen Sufficiency and Circulatory Parameters", Science, vol. 198, pp. 1264–1267.

*Primary Examiner*—Angela D. Sykes
*Assistant Examiner*—Eric F. Winakur
*Attorney, Agent, or Firm*—Cushman Darby & Cushman; IP Group of Pillsbury; Madison & Sutro LLP

[57] ABSTRACT

Optical pulses emitted from an optical pulse source is incident on a living tissue and is input to an optical sampling unit. An optical sampling unit detects intensities, f, of optical pulses detected at the respective timings of trigger signals input from a delay unit. A first accumulator calculates products, t·f, of the intensities f and the delay times t from the delay unit. A second accumulator accumulates the light intensities f. An average optical pathlength calculating unit calculates an average optical pathlength using the accumulation results as the products t·f and the intensities f. An $SO_2$ value calculating unit calculates a ratio of $V_{HbO2}$ to $V_{Hb}$ from the average optical pathlength to calculate an $SO_2$ value.

7 Claims, 11 Drawing Sheets

METHOD AND APPARATUS FOR MEASURING CONCENTRATION OF ABSORPTIVE CONSTITUENT IN SCATTERING MEDIUM

BACKGROUND OF THE INVENTION

1. Field of The Invention

The present invention relates to a method and apparatus for measuring the concentration of an absorptive constituent (e.g., hemoglobin) present in a scattering medium (e.g., a living tissue).

2. Related Background Art

When light having a wavelength near a near-infrared range is incident on living tissue, absorption of the incident light by the living tissue is greatly influenced by hemoglobin in blood. The influence of oxyhemoglobin ($HbO_2$) is different from that of deoxygenated hemoglobin (Hb). The absorption spectra of the living tissue changes in accordance with the states of hemoglobin, as shown in the graph in FIG. 1. The wavelength [nm] of incident light is plotted along the abscissa in FIG. 1, and the absorbance [$mM^{-1}cm^{-1}$] is plotted along the ordinate. As shown in this graph, the absorbance caused by deoxygenated hemoglobin (Hb) is higher than that by oxyhemoglobin ($HbO_2$) when the wavelength is shorter than 800 nm. When the wavelength is longer than 800 nm, the absorbance caused by oxyhemoglobin ($HbO_2$) is higher than that by deoxygenated hemoglobin (Hb). That is, the optical absorption in living tissue changes in accordance with the metabolic conditions of oxygen in the living tissue.

Conventionally, a monitor for oxygen metabolism in living tissue has been developed using this principle. Such a monitor has been put to practical use. In this oxygen metabolism monitor, however, the relative change since the start of measurement can only be monitored. For this reason, the degree ($SO_2$ value) of saturation of oxygen in blood in living tissue, which is a ratio of an oxyhemoglobin ($HbO_2$) concentration to a total hemoglobin concentration, cannot be measured. Therefore, the $SO_2$ value as the index of oxygen metabolism in the living tissue cannot be known. Therefore, an attempt has been made using the following method and apparatus to measure this $SO_2$ value.

First, a measuring apparatus (tradename: Cerebral Oximeter (invos 3100)) available from Somanetics is used as an apparatus for measuring an $SO_2$ value in blood in living tissue. This apparatus measures the concentration of an absorptive constituent (hemoglobin) in the scattering medium (living tissue) using the principle shown in FIG. 2. More specifically, continuous (CW) light having different wavelengths in the near-infrared range is incident on living tissue 1, and attenuation amounts of the incident light are detected at detection positions spaced apart from the light incident position by distances r1 and r2. The Hb and $HbO_2$ concentrations are obtained in accordance with the correlations between the attenuation amounts of incident light components having different wavelengths and the distances r1 and r2 between the light incident position and the detection positions, because the absorption profiles of incident light components in the living tissue is different as described above, thereby measuring the $SO_2$ value in blood.

Second, a spectroscopic technique for an absorptive constituent in a scattering medium using a time-resolved spectroscopy is available, as disclosed in U.S. Pat. No. 5,119,815 by B. Chance et al. This reference describes that the spectroscopic technique is applied to an $SO_2$ value measurement in blood of a living tissue. More specifically, an optical pulse is incident on the living tissue, and an optical pulse profile spreading as a function of time due to light scattering is time-resolved measured to obtain a profile representing a change in light intensity as a function of a change in time. Light absorption in the living tissue is measured such that the light intensity of the resultant profile is logarithmically calculated, and a gradient of the change in light intensity as a function of time is obtained. When time-resolved measurement is performed upon incidence of two optical pulses having different wavelengths on the living tissue, the light absorption for each optical pulse of each wavelength is measured, thereby the $SO_2$ value in the blood can be calculated, because the light absorption profiles of Hb and $HbO_2$ are different from each other.

Third, a spectroscopic technique for an absorptive constituent in a scattering medium, using phase modulation spectroscopy, is available, as disclosed in U.S. Pat. No. 4,972,331 by B. Chance et al. This reference describes that this spectroscopic technique can be applied to an SO., value measurement in blood. More specifically, modulated light is incident on the living tissue, and light absorption of the incident light is detected on the basis of a change in phase caused by propagation of the modulated light through the living tissue. When modulated light components having different wavelengths are incident on the living tissue, the concentration ratios of $HbO_2$ and Hb are detected to calculate the $SO_2$ value in the blood because the change in phase varies depending on the type of absorptive constituent in the living tissue and the wavelength of the incident modulated light.

SUMMARY OF THE INVENTION

The following problems are posed by the conventional measurements for concentrations of absorptive constituents in the scattering media.

The measuring apparatus available from Somanetics, as the first prior art, must have a plurality of photodetecting devices, thus resulting in a complicated device setup because the attenuation amounts of the incident light must be detected at a plurality of detection positions. In addition, conditions under which the respective photodetecting devices are brought into contact with a skin must be equal to each other. When a patient moves in contact with the photodetecting devices even under the equal conditions, photodetecting conditions of the respective devices may become nonuniform at the respective positions. That is, indefinite factors are included in optical measurements in this measuring device. It is, therefore, difficult to accurately measure an $SO_2$ value in blood.

In use of the time-resolved measurement as the second prior art, the total light intensity vs. time profile must be measured because the optical absorption of the incident light is detected in accordance with the gradient of the light intensity vs. time profile. For this reason, the calculation process for obtaining the $SO_2$ value from the measurement data becomes complicated, and a circuit arrangement required for this calculation process becomes bulky. In this measurement method, the number of wavelengths of the optical pulses incident on the living tissue is two, and the incident pulse light having each wavelength is time-resolved measured to calculate the $SO_2$ value in the blood. Such a two-wavelength measurement can be performed only when background absorption except for hemoglobin in the blood can be neglected. $H_2O$, proteins, and the like present in the living tissue except for the hemoglobin cannot be generally neglected with respect to incident light in the near-infrared range. Therefore, the concentration measurement of the absorptive constituents in the scattering medium, proposed by B. Chance et al., can be applied to only a limited number of scattering media so as to measure $SO_2$ values.

In the technique for measuring an $SO_2$ value using the frequency-resolved measurement method as the third prior art, it is expected that an optimal modulation frequency of the incident light may vary depending on scattering condition, boundary conditions, and the like in the living tissue. For this reason, the modulation frequency must be set again for each living tissue on which an optical pulse is incident. The optical measurement process cannot be simply performed. In addition, when the modulation frequency cannot be optimally set for the living tissue, an accurate $SO_2$ value cannot be measured. Even in this prior art using the modulated light, a two-wavelength infrared measurement is required. The background absorption cannot be neglected, as described above, and this technique can be applied to only a limited number of scattering media so as to measure the concentrations of absorptive constituents.

The present invention has been made to solve the conventional problems described above and includes the steps of causing light having a predetermined wavelength to be incident from a predetermined position of a scattering medium containing n (n≧2) types of absorptive constituents, detecting the light, scattering in the scattering medium at a predetermined position spaced apart from the light incident position by a predetermined distance, calculating an average optical pathlength of the light having the predetermined wavelength in the scattering medium on the basis of the detected light, obtaining respective average optical pathlengths of light components having n+1 types of wavelengths while a wavelength of light incident on the scattering medium is changed, obtaining respective average optical pathlength differences between respective pairs of light components having different wavelengths from the average optical path lengths, and obtaining a concentration ratio of the respective absorptive constituents in the scattering medium in accordance with a relationship representing that the average optical pathlength difference is inversely proportional to a difference in absorbance of the absorptive component between the light components having two wavelengths.

The present invention also includes a light source for generating pulsed light having a predetermined wavelength every predetermined time interval, light guide means for causing each pulse of light from the light source to be incident on a scattering medium containing n (n≧2) types of absorptive constituents from a predetermined position and extracting each pulse of light scattering within the scattering medium from a predetermined position spaced apart from the light incident position by a predetermined distance, photodetecting means for time-resolved measuring each pulse of light extracted by the light guide means, wavelength control means for controlling a wavelength of the pulses emitted from the light source, optical pathlength calculating means for calculating an average optical pathlength of light components having n+1 wavelengths in the scattering medium in accordance with time-resolved measurement results of pulse light components having n+1 wavelengths obtained by causing the wavelength control means to control the wavelength of the pulse light emitted from the light source, and concentration calculating means for obtaining an average optical pathlength difference between light components having two wavelengths from the average pathlengths calculated by the optical pathlength calculating means and obtaining a ratio of the absorptive constituent concentrations in the scattering medium in accordance with a relationship representing that the average optical pathlength difference is inversely proportional to a difference in absorbance of the absorptive component between the light components having two wavelengths.

According to the present invention, incident light scattering in a scattering medium can be detected at one location of the scattering medium. Therefore, detection of each incident light passing through the scattering medium can always be performed under the same conditions, and indefinite factors in the optical measurement process can be excluded. For this reason, the concentration measurement in the scattering medium can be accurately performed.

Even if background factors except for absorptive constituents serving as measurement targets are present in the scattering medium, the measurement is free from the influences of light absorption caused by these background factors. Therefore, the concentration measurement in a wide range of objects can be performed regardless of the types of scattering media.

Light incident on the scattering medium can be set independently of light scattering and the like in the scattering medium. For this reason, the conditions of the apparatus need not to be changed in accordance with the types of scattering media, and hence the conditions of the incident light need not to be set again. The concentration measurement of the absorptive constituent in the scattering medium can be easily and accurately performed.

DETAILED DESCRIPTION OF PREFERRED EMBODIMENTS

A method and apparatus for measuring the concentration of an absorptive constituent in a scattering medium according to the present invention will be described when they are applied to a measurement of Hb and $HbO_2$ concentrations in a blood of a living tissue. In principle, this concentration measurement comprises [1] a process for correlating an average optical pathlength in the scattering medium with light absorption information, [2] a process for measuring an average optical pathlength, [3] a process for acquiring light absorption information from an average optical pathlength difference between optical pulses having two different wavelengths, and [4] a process for deriving a ratio of absorptive constituent concentrations in the scattering medium from this light absorption information. These processes will be described in detail below.

Figure 3:
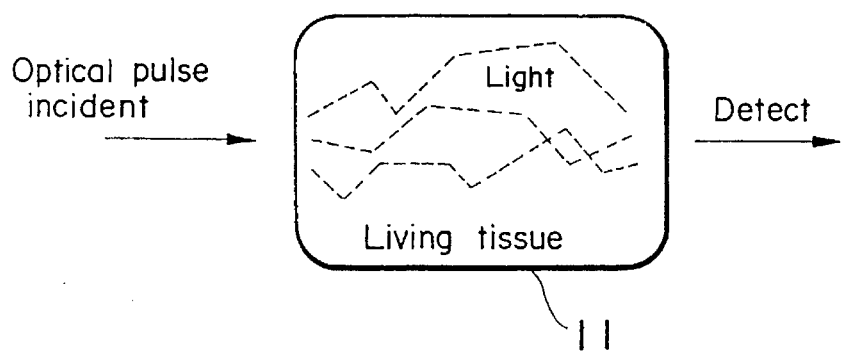
FIG. 3 shows that pulse light scatters in a living tissue spreading as a function of time and is detected.
Figure 4:
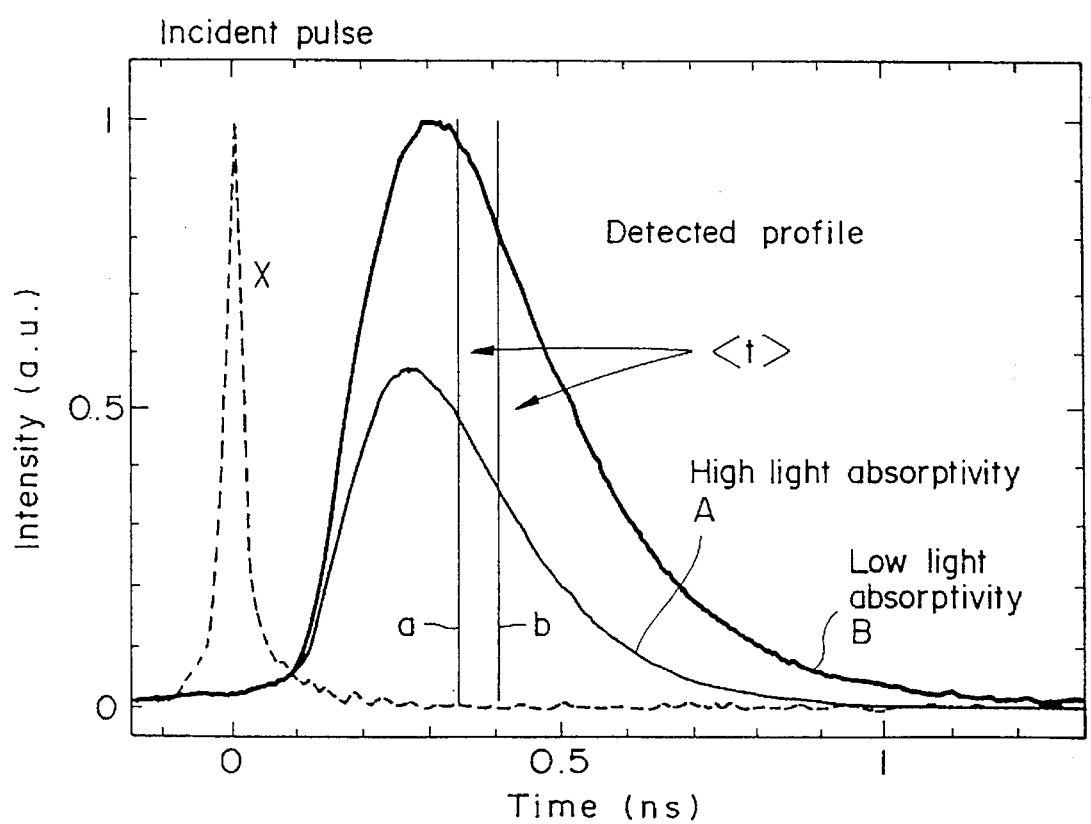
FIG. 4 shows a graph for explaining the principle of measurement of the present invention, representing a profile X of pulse light incident on a scattering medium and profiles A and B of pulse light components detected upon scattering and absorption of this pulse light in the scattering medium.

[1] Process for Correlating Average Optical Pathlength with Light Absorption Information As shown in FIG. 3, when an optical pulse is incident on a living tissue 11, the light pulse scatters as a function of time and is detected. The intensity of the optical pulse detected as described above has a profile shown in a graph in FIG. 4. Time [ns] is plotted along the abscissa in FIG. 4, and the detection light intensity [a.u.] is plotted along the ordinate therein. As shown in this graph, the average optical pathlength of the optical pulse between the optical pulse incident position and a detection position changes in accordance with an influence of light absorption in the living tissue. More specifically, when pulse light having a profile X indicated by a dotted line in FIG. 4 is incident on the living tissue, a detection profile is detected as a profile A when light absorption in the living tissue is high; when light absorption is low, the detection profile becomes a profile B. That is, a mean flight time $<t>$ during which the optical pulse passes through the living tissue changes in accordance with a light absorption state in the living tissue. This mean flight time $<t>$ corresponds to a time interval from an incident timing at zero time when the pulse light is incident to a barycentral position 8a or b of the profile A or B. As shown in this graph, when the light absorption is high, the mean flight time $<t>$ becomes short; when the light absorption is low, the mean flight time $<t>$ becomes long. The present inventors disclose in other patent applications (Japanese Patent Application No. 2-322105 and Japanese Patent Laid-Open No. 4-191642) that a detection intensity $f(t, \epsilon VC)$ actually measured for an incident optical pulse having such spreading as a function of time is represented as a product of a light intensity $f_0(t)$ in the absence of absorptive constituents in the scattering medium and a light intensity $10^{-\epsilon VCt}$ in the presence of absorptive constituents as follows:

$$f(t,\epsilon VC)=f_0(t)10^{-\epsilon VCt} \tag{1}$$

where t is the time from the optical pulse incident timing $\epsilon$ is the absorption coefficient of an absorptive constituent in the scattering medium, which varies depending on wavelengths of incident light components V is the molar concentration of the absorptive constituent C is the speed of light in the scattering medium Equation (1) is deemed to represent a photon distribution as a function of time until the photon reaches from the light incident position to the detection position. That is, this profile is a so-called scattering time profile. The parameters $\epsilon$, V, and C increase with respect to the scattering time profile $f_0(t)$ in the absence of light absorption. To simplify the calculation, the exponential base of 10 is replaced with e, and the exponential part $-\epsilon VCt$ is replaced with $-at$ to rewrite equation (1) into equation (2) as follows:

$$f(t,a)=f_0(t)e^{-at} \tag{2}$$

In this case, the absorption coefficient for the exponential base of $e$ is defined as $\epsilon'$, and $\epsilon VC=0.434\epsilon'VC=a$ is established.

An average optical pathlength $C<t(a)>$ required to cause the photon to reach the detection position from the light incident position is defined as equation (3) below:

$$C<t(a)> = \frac{C\int_0^\infty tf_0(t)e^{-at}dt}{\int_0^\infty f_0(t)e^{-at}dt} \tag{3}$$

The numerator and denominator of equation (3) are Taylor-expanded to approximate terms up to terms of the first degree around $a_0$, and the resultant equation is divided by an integral term represented by following expression:

$$\int_0^\infty f_0(t)e^{-a_0t}dt \tag{4}$$

Equation (5) can be obtained by the following equation transform. In this case, a Laplasian transform relation is used to derive equation (5), provided that $a=a_0+\Delta a$ is established:

$$\begin{aligned}
<t(a)> &= \frac{\int_0^\infty tf_0(t)e^{-at}dt}{\int_0^\infty f_0(t)e^{-at}dt} \\
&\approx \frac{\int_0^\infty tf_0(t)e^{-a_0t}dt - (a-a_0)\int_0^\infty t^2f_0(t)e^{-a_0t}dt}{\int_0^\infty f_0(t)e^{-a_0t}dt - (a-a_0)\int_0^\infty tf_0(t)e^{-a_0t}dt} \\
&= \frac{<t(a_0)> - (a-a_0)<t^2(a_0)>}{1-(a-a_0)<t(a_0)>} \\
\therefore <t(a)> &\approx \frac{<t(a_0)> - <t^2(a_0)>\Delta a}{1-<t(a_0)>\Delta a}
\end{aligned} \tag{5}$$

[2] Process for Measuring Average Optical Pathlength

Figure 5:
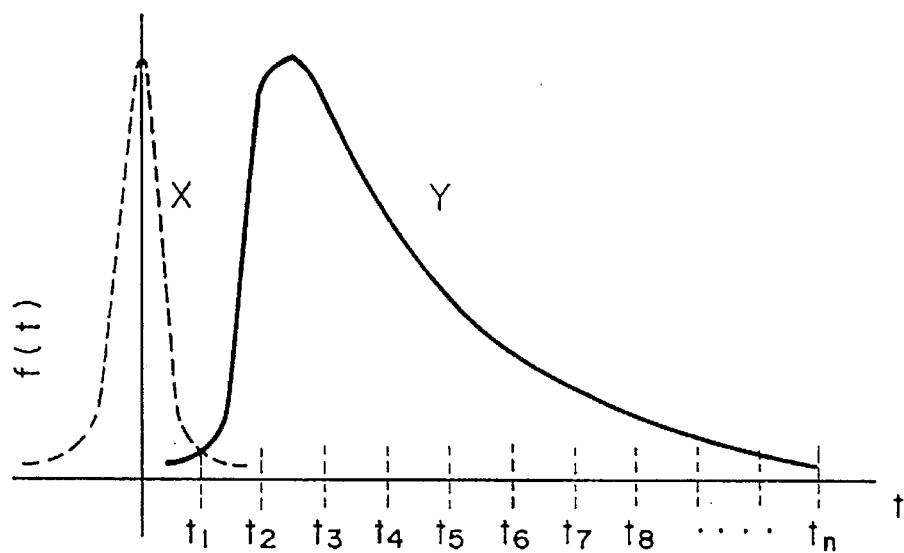
FIG. 5 is a graph showing sampling timings $t_n$ of a detected light profile Y when an average optical pathlength is expressed in the form of a sequence.

The average optical pathlength is defined by equation (3), but can be rewritten as equation (6) in the form of a sequence.

$$C<t(a)> = \frac{C \sum_n t_n f(t_n, a)}{\sum_n f(t_n, a)} \quad (6)$$

wherein times $t_n$ ($=t_1, t_2, t_3, \ldots$) can be plotted at a predetermined interval, as indicated in the graph of FIG. 5. Time t is plotted along the abscissa of this graph, and a light intensity f(t) is plotted along the ordinate thereof. This graph represents that an optical pulse having a profile X indicated by a dotted line is incident on a living tissue to obtain a detection profile Y.

The average optical pathlength C<t> is obtained from equation (6) as follows. That is, timings at which optical pulses are incident on the living tissue are given with delay times $t_n$ with reference to the incidence of the light having the profile X, and light intensities f($t_n$, εCV) are measured at the respective timings. The products of the light intensities f($t_n$,εCV) and delay times $t_n$, which are represented as the numerator of equation (6), are accumulated. The light intensities f($t_n$,εCV) represented by the denominator of equation (6) are accumulated. The sum of the numerator is divided by the sum of the denominator to obtain a quotient, thereby calculating the average optical path length C<t>.

The average optical pathlength can also be obtained in a single-photon measurement by equation (7) as follows:

$$C<t(a)> = \frac{C \sum_n^N T_n}{N} \quad (7)$$

where N is the number of measured photons.

Figure 6:
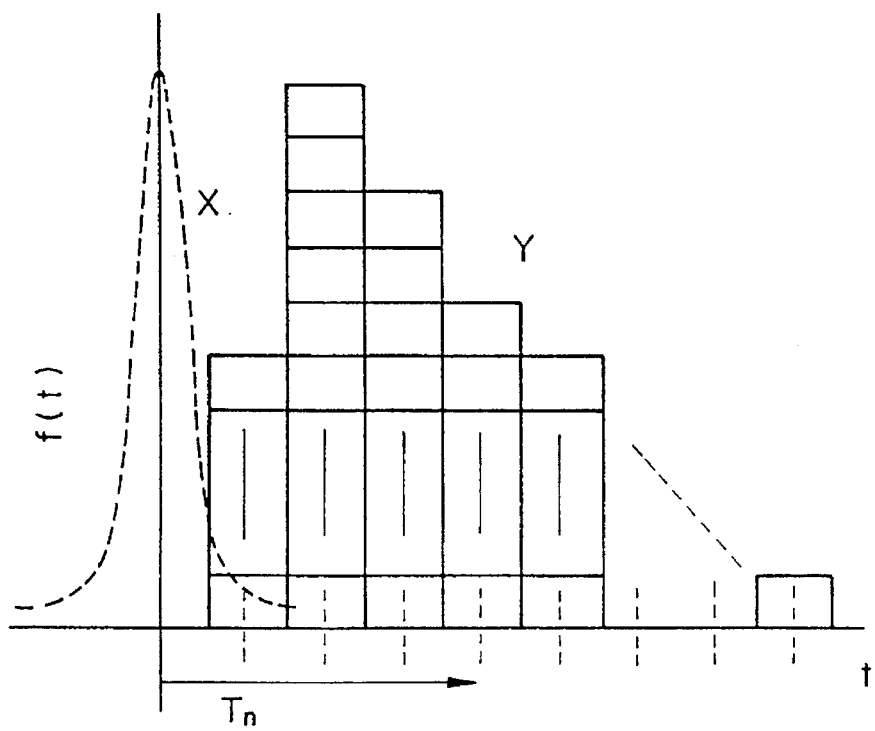
FIG. 6 is a graph showing a detected light profile Y obtained when a large number of photons are detected in single-photon measurements.

A detection profile shown in FIG. 6 is obtained according to this single-photon measurement. As in the graph of FIG. 5, time t is plotted along the abscissa, and the light intensity f(t) is plotted along the ordinate in FIG. 6. When an optical pulse having a profile X is incident on a living tissue, and a plurality of photons having different delay times from the optical pulse incident timing are respectively measured, a detection profile Y is obtained. The delay times from the incident timings of individual photons to their detection timings are accumulated, and the sum is divided by the total number N of photons, thereby calculating the average optical pathlength.

[3] PROCESS FOR ACQUIRING LIGHT ABSORPTION INFORMATION FROM AVERAGE OPTICAL PATHLENGTH DIFFERENCE

Light absorption information in the scattering medium is obtained from the resultant average optical pathlength as follows. That is, equation (5) is transformed into equation (8) below:

$$<t(a)>-<t(a)><t(a_0)>\Delta a=<t(a_0)>-<t^2(a_0)>)\Delta a \therefore <t(a)>-<t(a_0)>= \\ (<t(a)><t(a_0)>-<t^2(a_0)>)\Delta a \quad (8)$$

In this case, when an approximation is performed such that $<t(a)><t(a_0)>=<t(a_0)>^2$, equation (8) can be rewritten as equation (9) as follows:

$$<t(a)>-<t(a_0)>=(<t(a_0)>^2-<t^2(a_0)>)\Delta a \therefore <t(a)>-<t(a_0)>=P(a_0)\Delta a \quad (9)$$

for $P(a_0)=<t(a_0)>^2-<t^2(a_0)>$, wherein this $P(a_0)$ is negative.

When optical pulses having two different wavelengths λ1 and λ2 and equal scattering coefficients in the scattering medium, i.e., equal values $f_0(t)$, are incident on the living tissue, equation (10) can be derived from equation (9). In this case, the variable $a$ at the wavelength λ1, the constant $a_0$ at the wavelength λ1, the variable $a$ at the wavelength λ2, and the constant $a_0$ at the wavelength λ2 are defined as $a_{\lambda 1}$, $a_{0\lambda 1}$, $a_{\lambda 2}$, and $a_{0\lambda 2}$ respectively.

$$<t(a_{\lambda 1})>-<t(a_{0\lambda 1})>=P(a_{0\lambda 1})\Delta a_{80\ 1}$$

$$<t(a_{\lambda 2})>-<t(a_{0\lambda 2})>=P(a_{0\lambda 2})\Delta a_{\lambda 2} \quad (10)$$

In equations (10), $a_{0\lambda 1}$ and $a_{0\lambda 2}$ depend on scattering. If $a_{0\lambda 1}=a_{0\lambda 2}=a_0$, then $\Delta a_{\lambda 1}=a_{\lambda 1}-a_0$ and $\Delta a_{\lambda 2}=a_0$, thereby obtaining equation (11) as follows:

$$<t(a_{\lambda 2})>-<t(a_{\lambda 1})>=P(a_0)\cdot(a_{\lambda 2}-a_{\lambda 1}) \quad (11)$$

Since $\epsilon VC=\underline{a}$ is established, $a_{\lambda 1}=\epsilon_{\lambda 1}CV$ and $a_{\lambda 2}=\epsilon_{\lambda 2}CV$ where $\epsilon_{\lambda 1}$ is the absorption coefficient at the wavelength λ1, and $\epsilon_{\lambda 2}$ is the absorption coefficient at the wavelength λ2. When the exponential base is returned from $\underline{e}$ to 10, equation (11) can be rewritten as equation (12), provided that $P(a_0)$ with the exponential base of 10 is represented as $P'(a_0)$:

$$\{<t(\epsilon_{\lambda 2}CV)>-<t(\epsilon_{\lambda 1}CV)>\}=P'(a_0)(\epsilon_{\lambda 2}-\epsilon_{\lambda 1})VC \quad (12)$$

This equation (12) represents that the difference between the average optical pathlengths or the mean flight times of the optical pulses having two different wavelengths is inversely proportional to the absorbance in the scattering medium. Therefore, the light absorption information in the scattering medium can be obtained by calculating the average optical pathlength difference or the mean flight time difference.

[4] PROCESS FOR DERIVING RATIO OF ABSORPTIVE CONSTITUENT CONCENTRATIONS IN SCATTERING MEDIUM

A concentration ratio of the absorptive constituents in the scattering medium, i.e., the $SO_2$ value in the blood of the living tissue, is obtained from the average optical pathlength difference calculated as described above. For this purpose, a concentration ratio of oxyhemoglobin ($HbO_2$) to deoxygenated hemoglobin (Hb) must be obtained. Two average optical pathlength differences represented by equation (12) must be calculated, and measurements of the average optical pathlengths at least three wavelengths (λ1, λ2, and λ3) must be performed. The absorption coefficients of $HbO_2$ and Hb at the respective wavelengths are summarized in Table 1 below.

TABLE 1

| Wavelength | $HbO_2$ | Hb |
|---|---|---|
| λ1 | $\epsilon_{HbO2,\lambda 1}$ | $\epsilon_{Hb,\lambda 1}$ |
| λ2 | $\epsilon_{HbO2,\lambda 2}$ | $\epsilon_{Hb,\lambda 2}$ |
| λ3 | $\epsilon_{HbO2,\lambda 3}$ | $\epsilon_{Hb,\lambda 3}$ |

Assume that the $HbO_2$ and Hb concentrations in the living tissue, and the mean flight times during which the optical pulses at the wavelengths λ1, λ2, and λ3 pass through the living tissue, are defined as $V_{HbO2}$, $V_{Hb}$, $<t>_{\lambda 1}$, $<t>_{\lambda 2}$, and $<t>_{\lambda 3}$, respectively. Light absorption is also present due to background factors except for hemoglobin in the living tissue. Assume light absorption values caused by these background factors at the wavelengths λ1, λ2, and λ3 are defined as $\alpha_{\lambda 1}$, $\alpha_{\lambda 2}$, and $\alpha_{\lambda 3}$, respectively. At this time, light absorption $a_{\lambda 1}$, $a_{\lambda 2}$, and $a_{\lambda 3}$ upon incidence of the pulse light components having the wavelengths λ1, λ2, and λ3 are defined by equations (13) below:

$$a_{\lambda 1} = (\epsilon_{HbO2,\lambda 1} \cdot V_{HbO2} + \epsilon_{Hb,\lambda 1} \cdot V_{Hb} + \alpha_{\lambda 1})C \quad (13)$$

$$a_{\lambda 2} = (\epsilon_{HbO2,\lambda 2} \cdot V_{HbO2} + \epsilon_{Hb,\lambda 2} \cdot V_{Hb} + \alpha_{\lambda 2})C$$

$$a_{\lambda 3} = (\epsilon_{HbO2,\lambda 3} \cdot V_{HbO2} + \epsilon_{Hb,\lambda 3} \cdot V_{Hb} + \alpha_{\lambda 3})C$$

Equation (12) can be rewritten as equation (14) below. In this case, assume the background absorption values in the living tissue at the wavelengths $\lambda 1$, $\lambda 2$, and $\lambda 3$ are equal to each other ($\alpha_{\lambda 1}=\alpha_{\lambda 2}=\alpha_{\lambda 3}$).

$$\begin{aligned}
<t>_{\lambda 2} - <t>_{\lambda 1} &= P'(a_0)\{(\varepsilon_{HbO2,\lambda 2} - \varepsilon_{HbO2,\lambda 1})V_{HbO2} + \\
&\quad (\varepsilon_{Hb,\lambda 2} - \varepsilon_{Hb,\lambda 1})V_{Hb}\}C \\
<t>_{\lambda 3} - <t>_{\lambda 1} &= P'(a_0)\{(\varepsilon_{HbO2,\lambda 3} - \varepsilon_{HbO2,\lambda 1})V_{HbO2} + \\
&\quad (\varepsilon_{Hb,\lambda 3} - \varepsilon_{Hb,\lambda 1})V_{Hb}\}C
\end{aligned} \quad (14)$$

In this case, if $<t>_{\lambda 2}-<t>_{\lambda 1}=\Delta<t>_{\lambda 2,\lambda 1}$ and $<t>_{\lambda 3}-<t>_{\lambda 1}=\Delta<t>_{\lambda 3,\lambda 1}$, equations (15) can be derived as follows:

$$(\varepsilon_{HbO2,\lambda 2} - \varepsilon_{HbO2,\lambda 1})V_{HbO2} + (\varepsilon_{Hb,\lambda 2} - \varepsilon_{Hb,\lambda 1})V_{Hb} = \quad (15)$$
$$\Delta<t>_{\lambda 2,\lambda 1}/P'(a_0)C$$

$$(\varepsilon_{HbO2,\lambda 3} - \varepsilon_{HbO2,\lambda 1})V_{HbO2} + (\varepsilon_{Hb,\lambda 3} - \varepsilon_{Hb,\lambda 1})V_{Hb} =$$
$$\Delta<t>_{\lambda 3,\lambda 1}/P'(a_0)C$$

Equations (15) are solved as simultaneous equations using $V_{HbO2}$ and $V_{Hb}$ as unknown values to obtain the following equations (16):

$$\begin{aligned}
P'(a_0)V_{HbO2} &= \{(\varepsilon_{Hb,\lambda 3} - \varepsilon_{Hb,\lambda 1})\Delta<t>_{\lambda 2,\lambda 1} \\
&\quad -(\varepsilon_{Hb,\lambda 2} - \varepsilon_{Hb,\lambda 1})\Delta<t>_{\lambda 3,\lambda 1}\}/D \\
P'(a_0)V_{Hb} &= \{-(\varepsilon_{HbO2,\lambda 3} - \varepsilon_{HbO2,\lambda 1})\Delta<t>_{\lambda 2,\lambda 1} \\
&\quad +(\varepsilon_{HbO2,\lambda 2} - \varepsilon_{HbO2,\lambda 1})\Delta<t>_{\lambda 3,\lambda 1}\}/D
\end{aligned} \quad (16)$$

In this case, D is represented as follows:

$$\begin{aligned}
D &= \{(\varepsilon_{HbO2,\lambda 2} - \varepsilon_{Hb,\lambda 1})(\varepsilon_{Hb,\lambda 3} - \varepsilon_{Hb,\lambda 1}) \\
&\quad - (\varepsilon_{Hb,\lambda 2} - \varepsilon_{Hb,\lambda 1})(\varepsilon_{HbO2,\lambda 3} - \varepsilon_{HbO2,\lambda 1})\}C
\end{aligned} \quad (17)$$

The ratio of the oxyhemoglobin concentration $V_{HbO2}$ to the deoxyhemoglobin $V_{Hb}$ can be obtained from equations (16) as follows:

$$\begin{aligned}
V_{HbO2}:V_{Hb} &= \{(\varepsilon_{Hb,\lambda 3} - \varepsilon_{Hb,\lambda 1})\Delta<t>_{\lambda 2,\lambda 1} - \\
&\quad (\varepsilon_{Hb,\lambda 2} - \varepsilon_{Hb,\lambda 1})\Delta<t>_{\lambda 3,\lambda 1}\}:\{-(\varepsilon_{HbO2,\lambda 3} - \\
&\quad \varepsilon_{HbO2,\lambda 1})\Delta<t>_{\lambda 2,\lambda 1} + \\
&\quad (\varepsilon_{HbO2,\lambda 2} - \varepsilon_{HbO2,\lambda 1})\Delta<t>_{\lambda 3,\lambda 1}\}
\end{aligned} \quad (18)$$

The degree ($SO_2$ value) of saturation of oxygen is calculated as follows:

$$SO_2 = V_{HbO2}/(V_{HbO2}+V_{Hb}) = 1/(1+V_{Hb}/V_{HbO2}) \quad (19)$$

A ratio of $V_{HbO2}$ to $V_{Hb}$ is obtained from equation (18), and a substitution of this concentration ratio in equation (19) can yield the degree of saturation of oxygen.

The preferred embodiments of the present invention using the above principle of measurement will be described below.

Figure 7:
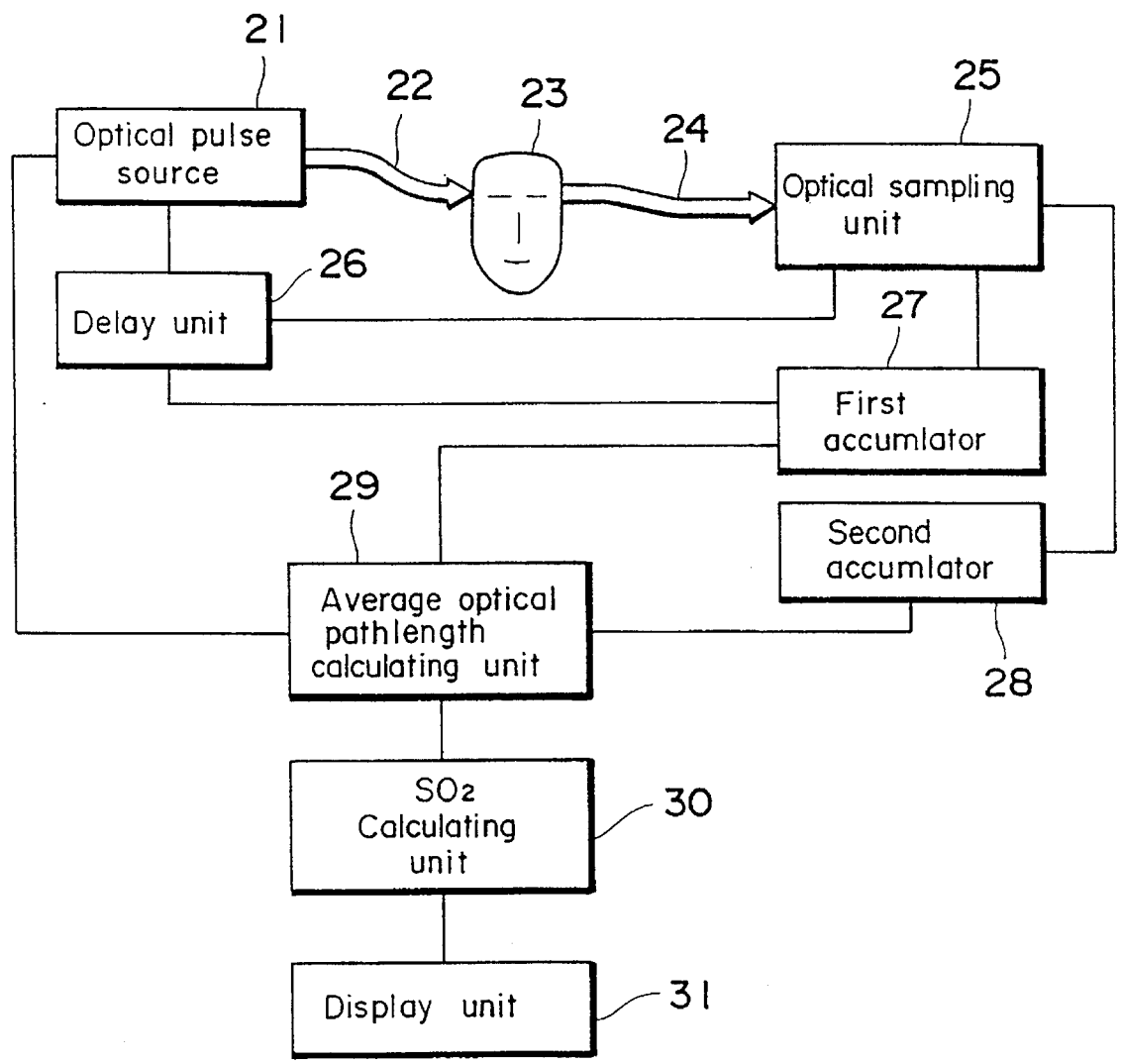
FIG. 7 is a block diagram showing the schematic arrangement of a light intensity sampling apparatus according to the first embodiment of the present invention.
Figure 8:
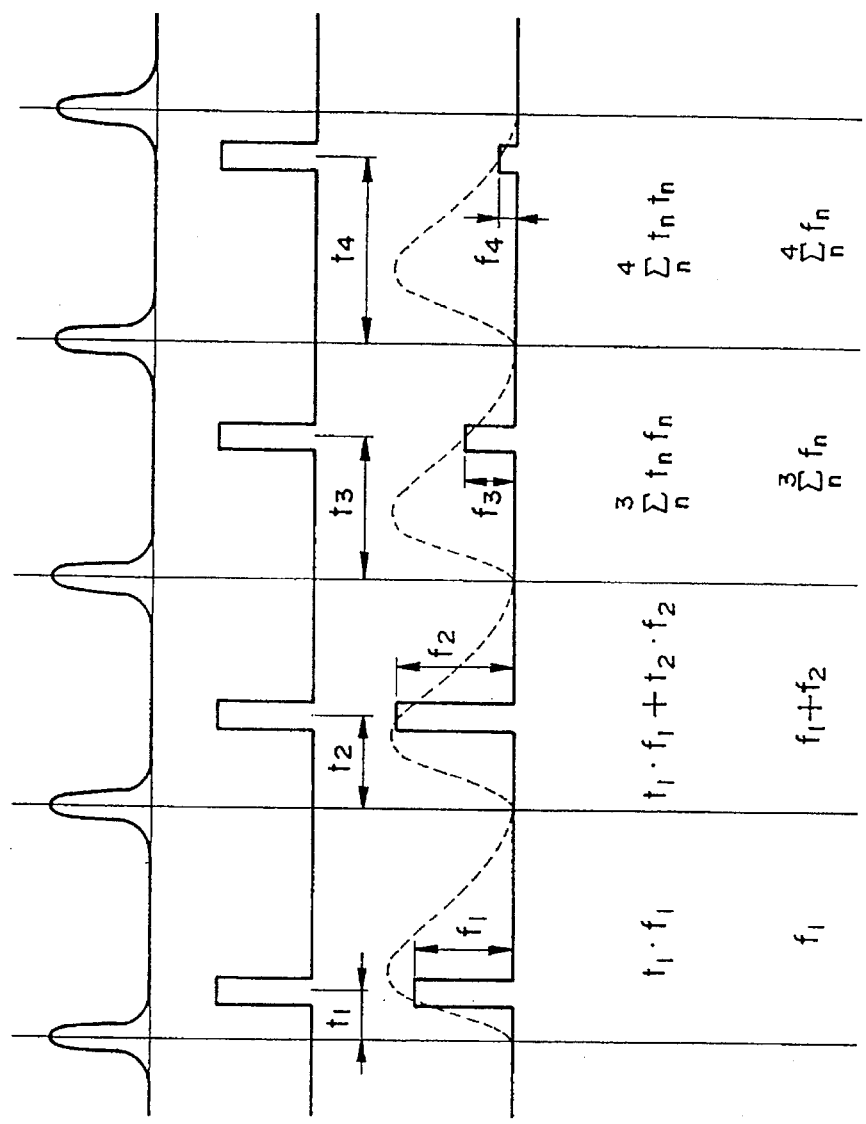
FIGS. 8(a)–8(e) are timing charts showing signals in the respective components of the light intensity sampling apparatus according to the first embodiment.

FIG. 7 is a block diagram showing the schematic arrangement of a light intensity sampling apparatus according to the first embodiment of the present invention. This light intensity sampling apparatus measures hemoglobin concentrations in the living tissue. This apparatus will be described with reference to the timing chart in FIG. 8.

An optical pulse source 21 emits an optical pulse having a predetermined wavelength $\lambda 1$ at a predetermined time interval (see FIG. 8(a)). The emitted optical pulse is incident on a living tissue 23 through an optical fiber 22 or directly. The optical pulse spreading as a function of time due to light scattering in the living tissue 23 is input to an optical sampling unit 25 directly or through an optical fiber 24. The optical pulse source 21 outputs a trigger signal to a delay unit 26 at an optical pulse emission timing. The delay unit 26 delays the input trigger signal by a predetermined period of time and outputs the delayed trigger signal to the optical sampling unit 25. This delay time is appropriately changed in each optical pulse. That is, the delay time changes in an order of $t_1$, $t_2$, $t_3$, $t_4$, ... with reference to the optical pulse emission timings (see FIG. 8(b)).

The optical sampling unit 25 receives each delayed trigger signal from the delay unit 26. At the respective sampling timings when the corresponding delayed trigger signals are input, the optical sampling unit 25 detects intensities $f_1$, $f_2$, $f_3$, $f_4$, ... of the optical pulses emitted from the optical pulse source 21 and passing through the living tissue 23 (see FIG. 8(c)). The delay unit 26 outputs the delay time of each delayed trigger signal to a first accumulator 27. The first accumulator 27 calculates a product t·f of the detected light intensity f supplied from the optical sampling unit 25 and the delay time t supplied from the delay unit 26 at each sampling timing. Such products t·f are accumulated ($t_1·f_1+t_2·f_2+t_3·f_3+t_4·f_4, \ldots$), and the sum is output to an average optical pathlength calculating unit 29 (see FIG. 8(d)). A second accumulator 28 receives the intensities f of the optical pulses, detected through the living tissue 23, from the optical sampling unit 25. The received intensities f are accumulated at the respective sampling timings ($f_1+f_2+f_3+f_4, \ldots$), and the sum is output to the average optical pathlength calculating unit 29. (see FIG. 8(e)).

The average optical pathlength calculating unit 29 calculates an average optical pathlength based on equation (6) using the sum of the products t·f input from the first accumulator 27 and the sum of the light intensities f input from the second accumulator 28. This average optical pathlength is obtained from an optical pulse spreaded and detected as a function of time upon incidence of the optical pulse having the predetermined wavelength $\lambda 1$ on the living tissue 23. The average optical pathlength calculating unit 29 outputs a control signal to the optical pulse source 21 to change the wavelength of an optical pulse emitted from the optical pulse source 21. By this wavelength control, the above calculation processes are also performed for the wavelengths $\lambda 2$ and $\lambda 3$ of the optical pulses, and the average optical pathlength calculating unit 29 also calculates average optical pathlengths for these wavelengths $\lambda 2$ and $\lambda 3$.

An $SO_2$ value calculating unit 30 receives the average optical pathlength calculation results for the wavelengths $\lambda 1$, $\lambda 2$, and $\lambda 3$ and calculates a ratio of the oxyhemoglobin concentration $V_{HbO2}$ to the deoxyhemoglobin concentration $V_{Hb}$ in the blood of the living tissue on the basis of equation (18). The resultant concentration ratio is substituted into equation (19) to calculate an $SO_2$ value in the blood. This $SO_2$ value is displayed on a display unit 31.

According to this embodiment, the pulse light emitted from the optical pulse source 21 and scattering in the living tissue 23 is detected at one location of the living tissue 23. Unlike the conventional measuring apparatus available from Somanetics, incident pulse light need not to be detected at the plurality of positions of the scattering medium. For this reason, once the pulse light incident position and the incident pulse light detection position are set, the respective pulse light components can always be detected under the same conditions. The measurement is free from influences of a contact state of a photodetecting unit with a skin and a motion of the living tissue. Therefore, the concentration measurements can always be accurately performed.

Even if background factors such as $H_2O$ and proteins except for hemoglobin are present, the measurement is free from the influences of light absorption caused by these factors. A ratio of $HbO_2$ to $Hb$ in the living tissue can be obtained without receiving these influences. For this reason, according to this embodiment, the concentrations of absorptive constituents in a wide range can be measured without influencing the types of scattering means.

Pulse light incident on the living tissue 23 can be set independently of light scattering in the scattering medium. Unlike the prior art disclosed in U.S. Pat. No. 4,972,331, the apparatus need not to be reset depending on the types of scattering media as measurement targets or the incident pulse light conditions need not to be changed. For this reason, the concentration measurement of the absorptive constituent in the living tissue can be facilitated, and a problem posed by inappropriate setup of the apparatus to lead to an inaccurate concentration measure can be prevented.

Figure 9:
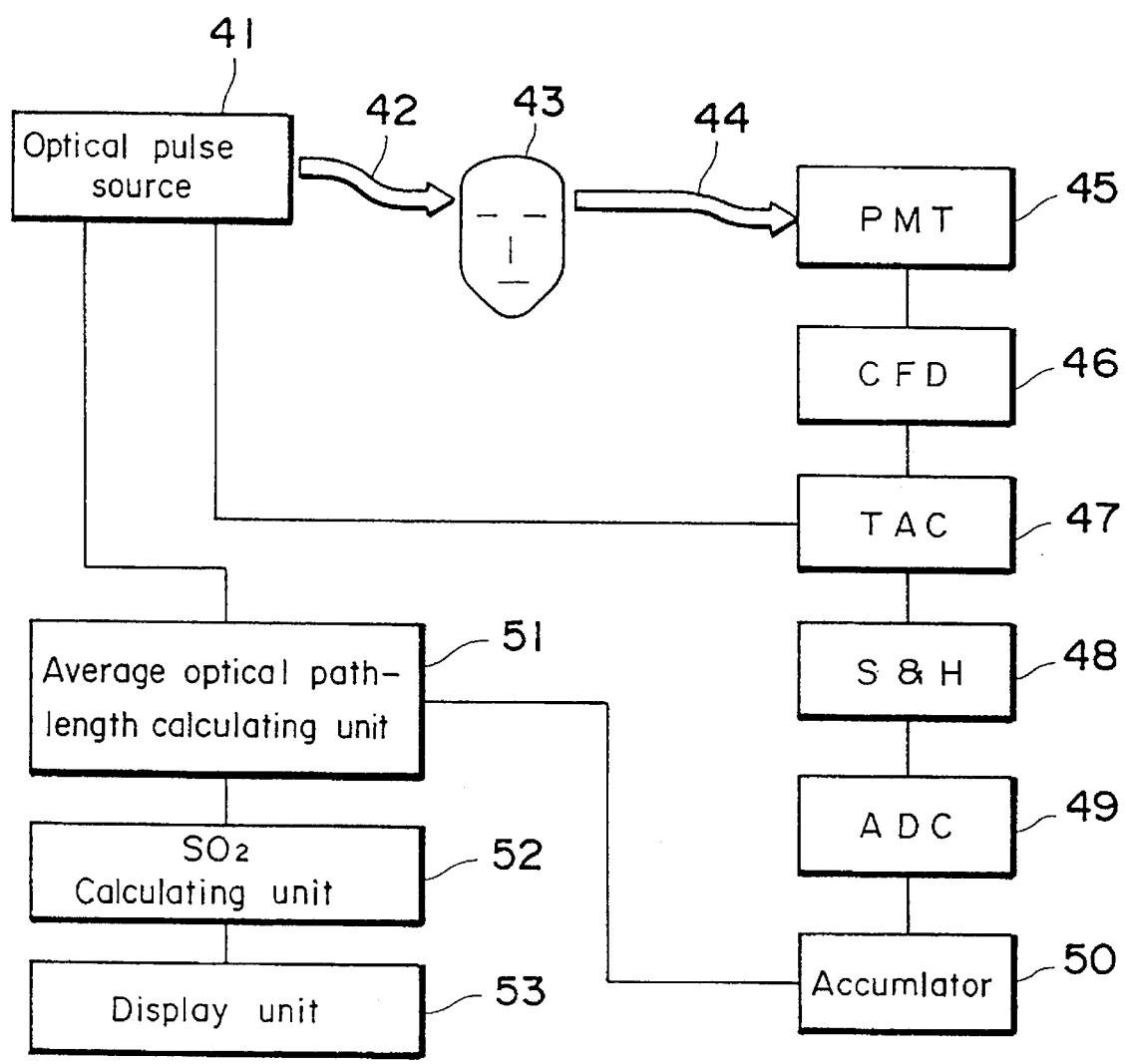
FIG. 9 is a block diagram showing the schematic arrangement of a light intensity sampling apparatus according to the second embodiment of the present invention.
Figure 10:
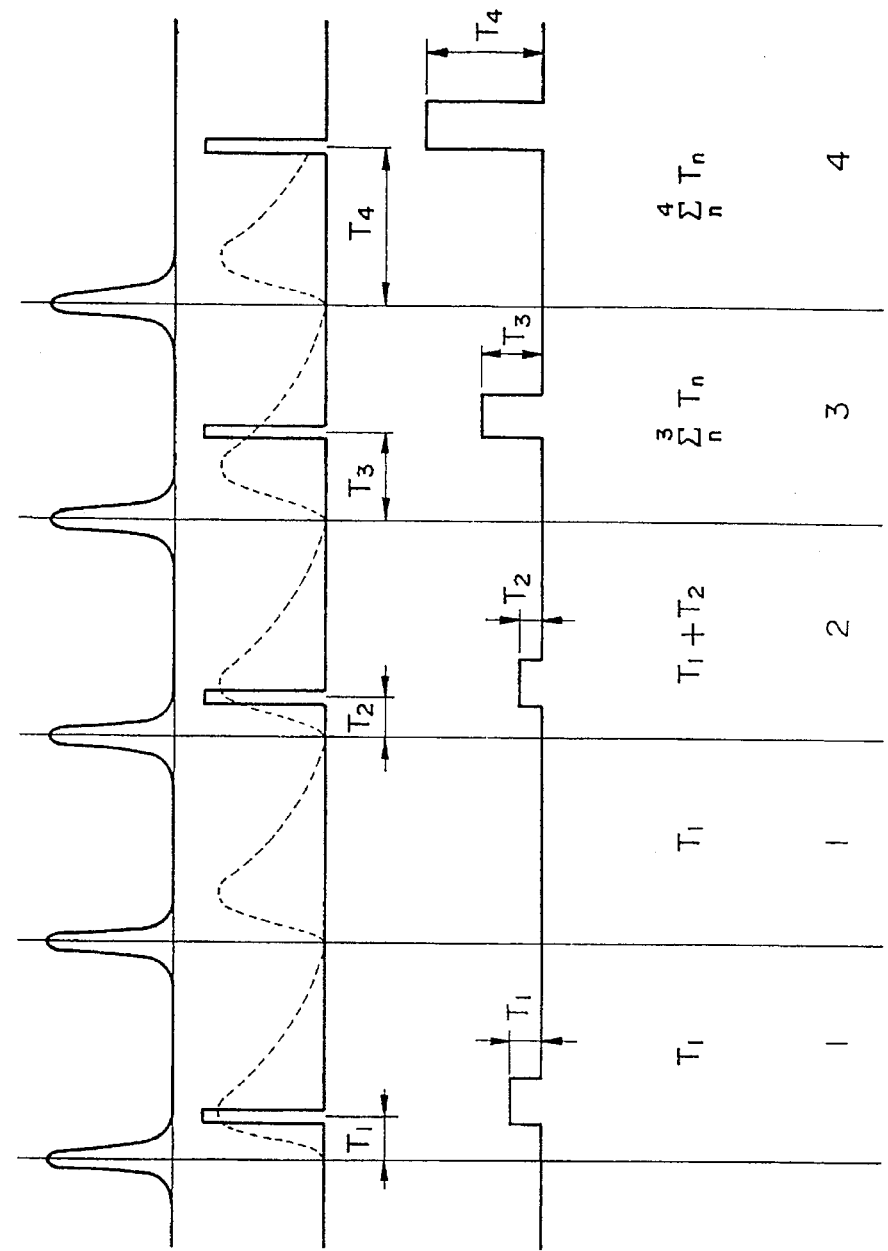
FIGS. 10(a)≧10(e) are timing charts showing signals in the respective components of the light intensity sampling apparatus according to the second embodiment.

A concentration measurement of absorptive constituents in a scattering medium according to the second embodiment of the present invention will be described below. FIG. 9 is a block diagram showing the schematic arrangement of a light intensity sampling unit according to the second embodiment, and this unit will be described with reference to FIG. 10.

An optical pulse source 41 emits an optical pulse having a predetermined wavelength $\lambda 1$ at a predetermined time interval (see FIG. 10(a)). The emitted light pulse is incident on a living tissue 43 through an optical fiber 42 or directly. The light pulse propagating through the living tissue 43 is input to a photomultiplier tube (PMT) 45 through an optical fiber 44 or directly. When the optical pulse emitted from the optical pulse source 41 is input to this PMT 45, no more than one photon must be detected per optical pulse single photon event. This one photon is converted into an electrical pulse signal by the PMT 45.

This electrical pulse signal is input to a constant fraction discriminator (CFD) 46 and the timing signal is picked off. The photons detected by the PMT 45 have different delay times from the optical pulse emission timings for the respective optical pulses. The CFD 46 outputs pulse signal (see FIG. 10(b)) delayed from the optical pulse emission timing by times $T_1, T_2, T_3, T_4, \ldots$ Note that a waveform indicated by a dotted line in FIG. 10(b) represents the profile of detection optical pulses obtained upon detection of a large number of photons. This profile represents spreading of the input optical pulse as a function of time.

The output pulse from the CFD 46 is supplied to a time to amplitude converter (TAC) 47. A timing signal is supplied to the TAC 47 when the optical pulse is emitted from the optical pulse source 41. The TAC 47 converts time differences between the timings of optical pulses incident on the living tissue 43 and the detection timings of the optical pulses in the PMT 45 on the basis of the pulse signals from the CFD 46 and the timing signals from the optical pulse source 41. That is, the TAC 47 outputs a pulse signal having an amplitude corresponding to each time difference (see FIG. 10(c)).

A sample & hold (S & H) circuit 48 receives an output pulse from the TAC 47 to detect and hold the peak value of this signal. An analog-to-digital converter (ADC) 49 converts this peak value into a digital signal. This value corresponds to each of the amplitudes $T_1$ to $T_4$ (see FIG. 10(c)) of the electrical pulse signals. An accumulator 50 accumulates these digital values $(T_1+T_2+T_3+T_4, \ldots)$ to obtain the sum of the amplitude values of the respective electrical pulse signals (see FIG. 10(d)). The accumulator 50 counts the number of electrical pulse signals output from the TAC 47 in addition to the above accumulation (see FIG. 10(e)). These accumulation values are output to an average optical pathlength calculating unit 51.

The average optical pathlength calculating unit 51 divides the sum of the amplitudes of the respective electrical pulse signals, i.e., the sum total of the photon detection delay times, by the total photon count to obtain a quotient, and outputs this quotient as an average optical pathlength to an $SO_2$ calculating unit 52. The average optical pathlength calculating unit 51 outputs a control signal to the optical pulse source 41 to change the wavelength of each optical pulse emitted from the optical pulse source 41. The above calculation processes are also performed for the wavelengths $\lambda 2$ and $\lambda 3$ of the optical pulses, and the average optical pathlength calculating unit 51 also calculates the average optical pathlengths for the wavelengths $\lambda 2$ and $\lambda 3$. The $SO_2$ calculating unit 52 receives the average optical pathlength calculation results of the wavelengths $\lambda 1$, $\lambda 2$, and $\lambda 3$ and calculates a ratio of an oxyhemoglobin concentration $V_{HbO2}$ to a deoxyhemoglobin concentration $V_{Hb}$ in the blood of the living tissue, on the basis of equation (18). The resultant concentration ratio is substituted into equation (19) to obtain an $SO_2$ value. The $SO_2$ value is output to a display unit 53. The display unit 53 displays the input $SO_2$ value.

The same effect as in the first embodiment can be obtained in the second embodiment. The degree of saturation of oxygen in the blood of the living tissue can be easily and accurately measured with a simple apparatus arrangement.

Figure 11:
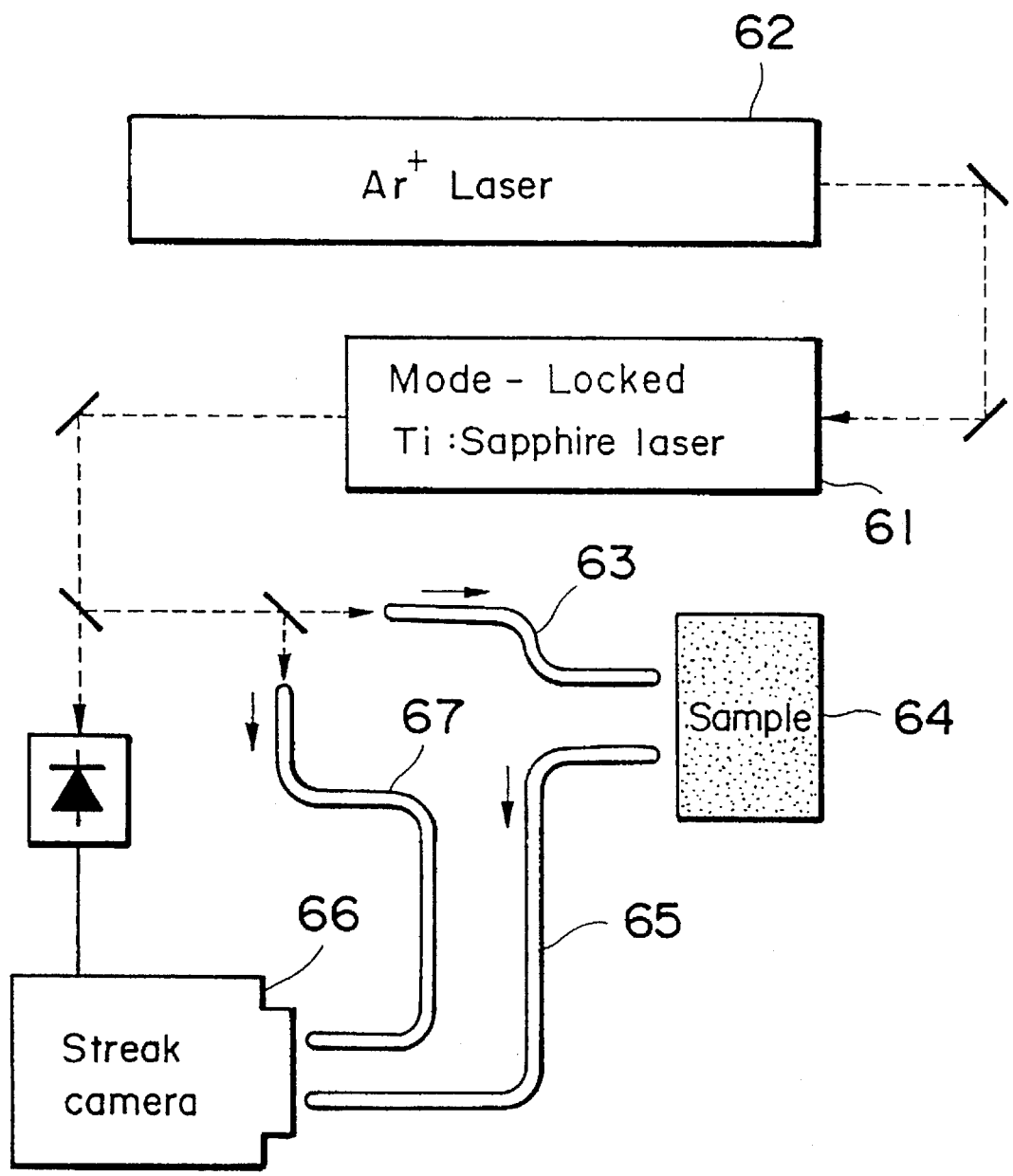
FIG. 11 is a block diagram showing the schematic arrangement of a light intensity sampling apparatus according to the third embodiment of the present invention.

The third embodiment will be described below in which a concentration measurement of absorptive constituents in a scattering medium is applied to a rat. FIG. 11 is a schematic block diagram of a concentration measuring apparatus according to the third embodiment.

A mode-locked Ti:Sapphire laser 61 is a pico-second optical pulse source and is excited by an output from an $Ar^+$ laser 62. In this embodiment, laser pulse light (pulse width: 2 pS or less) having a repetition frequency of 76 MHz within the wavelength range of 730 to 860 nm is output from the mode-locked Ti:Sapphire laser 61. This pulse light is incident on a sample 64 through an optical fiber 63. The pulse light diffusively reflected by or passing through the sample 64 is input to a streak camera 66 through an optical fiber 65. At the same time, the pulse light output from the Ti:Sapphire laser 61 is input to the streak camera 66 through the optical fiber 67 without going through the sample 64. In this embodiment, the pulse light incident on the sample 64 is time-resolved measured by the streak camera 66.

Figure 12:
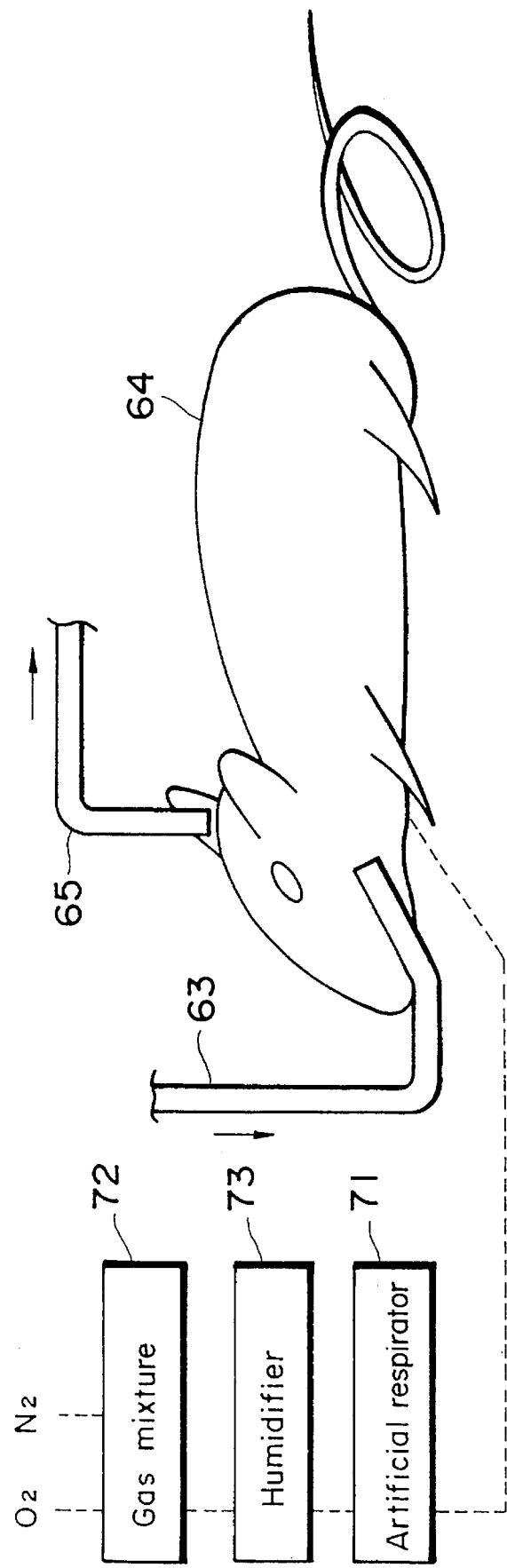
FIG. 12 is a view showing a rat serving as a sample used in the third embodiment.

The sample 64 is a Wistar rat shown in FIG. 12. The pulse light incident optical fiber 63 is inserted into the oral cavity of the rat 64. The pulse light detection optical fiber 65 is located at the parietal portion of the rat 64. This rat 64 is anesthetized with nembutal, and a tracheal cannula is inserted into a trachea. An artificial respirator 71 is connected to the tracheal cannula. A gas mixture of $O_2$ and $N_2$ mixed by a gas mixture 72 and dampened by a humidifier 73 is supplied to this artificial respirator 71. In artificial respiration, the oxygen concentration ($FiO_2$) in the inhalation gas to the rat 64 is adjusted, so that the amount of oxygen supplied to the rat 64 is controlled.

Figure 13:
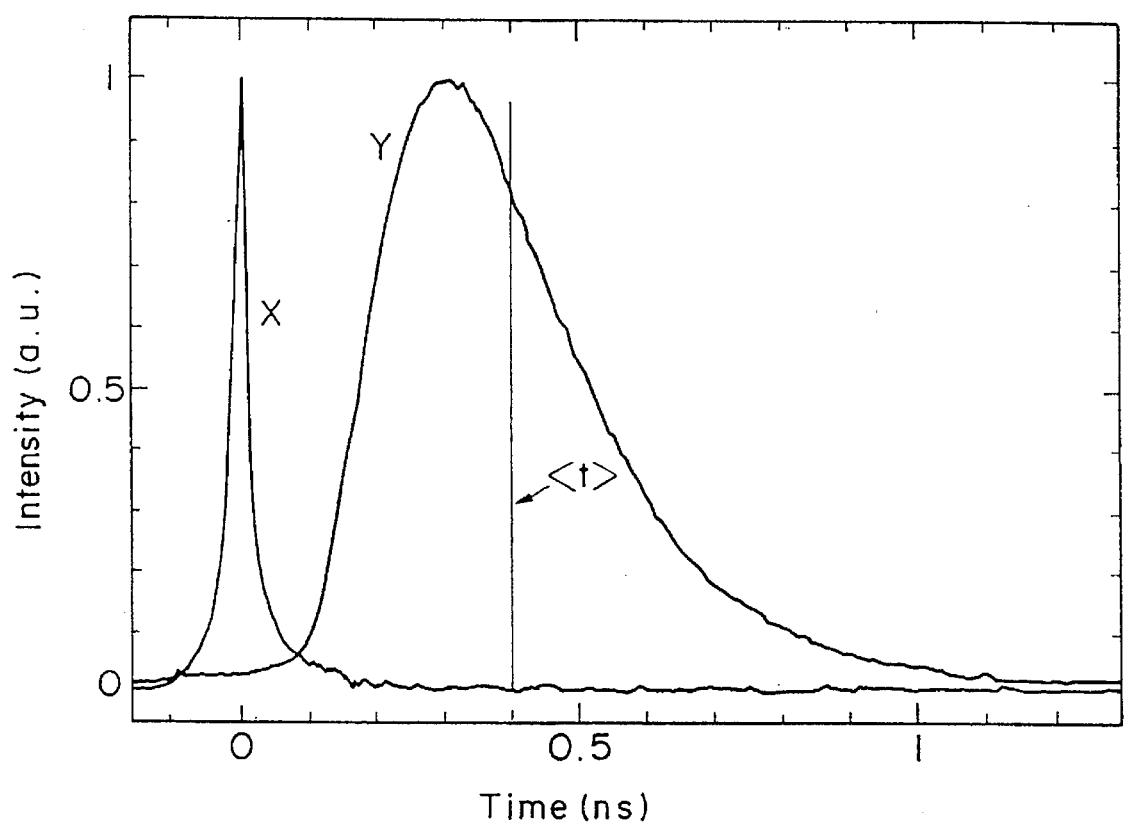
FIG. 13 is a graph showing the profiles of incident pulse light and detected pulse light in the third embodiment.

In this apparatus arrangement, pulse light incident from the Ti:Sapphire laser 61 on the rat 64 and pulse light detected by the streak camera 66 have profiles as shown in the graph of FIG. 13. Time [ns] is plotted along the abscissa of this graph, and the detection light intensity [a.u.] is plotted along the ordinate thereof. A profile X is a profile of pulse light incident into the oral cavity of the rat 64, and a profile Y is a profile of detection light spreading in the head. A mean flight time <t> between the timing of incidence of the pulse light on the rat 64 and the detection timing corresponds to a time <t> between zero time and the barycentral position of the profile Y. An average optical pathlength C<t> obtained by multiplying a mean flight time <t> with a speed of light C is obtained on the basis of equation (6) described above. This average optical pathlength measurement was performed while the wavelength of the pulse light incident on the rat 64 was changed within the range of 740 to 820 nm. The oxygen concentration FiO$_2$ in the inhalation gas supplied to the rat 64 was changed in orders of 100%, 20%, and 15%.

Figure 1:
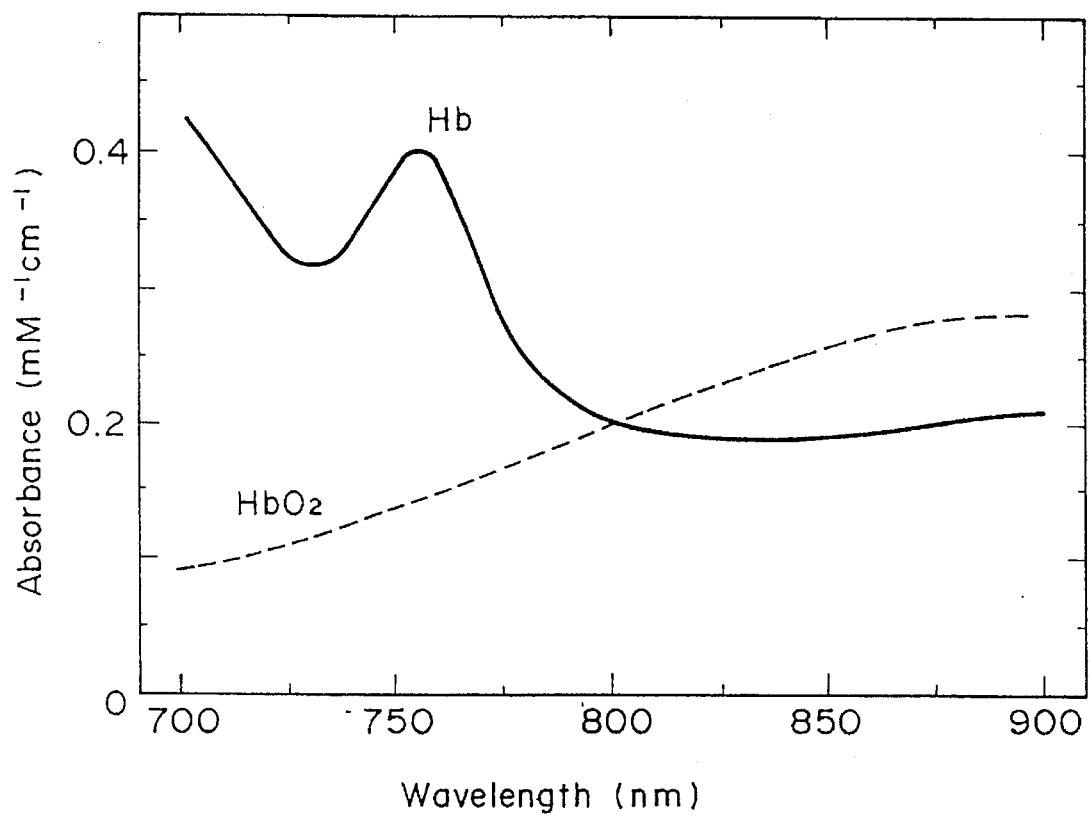
FIG. 1 is a graph showing the light absorption profiles of deoxygenated hemoglobin Hb and oxyhemoglobin $HbO_2$.
Figure 2:
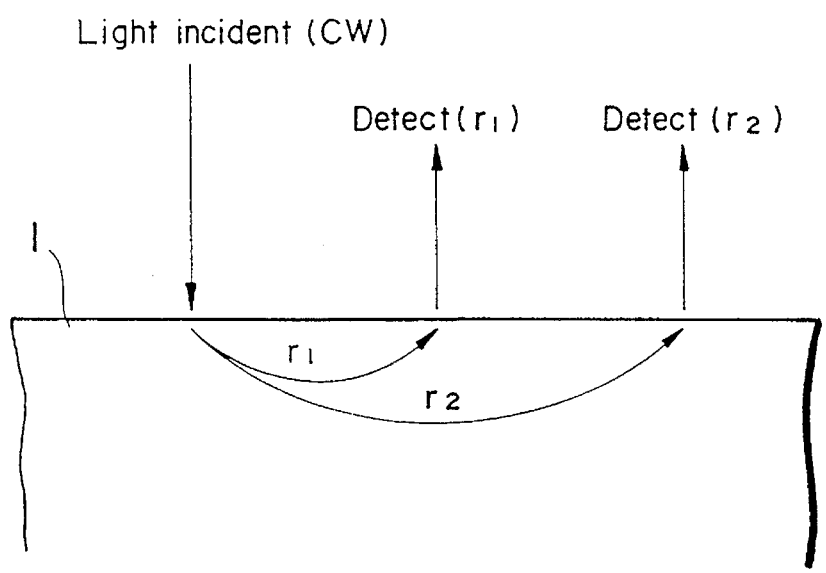
FIG. 2 is a sectional view showing a living tissue for explaining the conventional principle of measuring the concentration of an absorptive constituent in a scattering medium.
Figure 14:
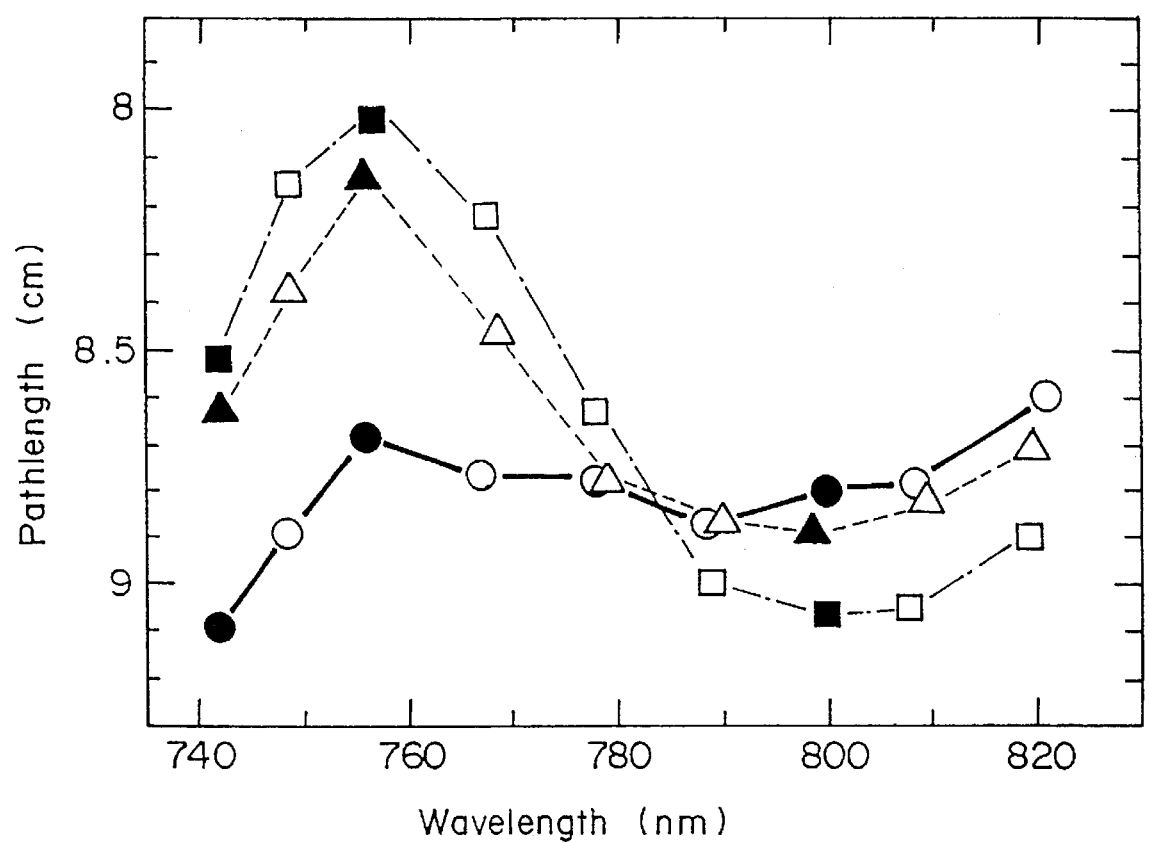
FIG. 14 is a graph showing changes in average optical pathlength with changes in wavelength of incident pulse light when an $FiO_2$ concentration in an inhalation gas supplied to the rat is used as a parameter.

FIG. 14 is a graph showing the measurement results. The wavelength [nm] of the incident pulse light is plotted along the abscissa, and the average optical pathlength [cm] is plotted along the ordinate. This average optical pathlength is calculated on the basis of equation (6) using the value of the speed of light C and has a value of 0.022 cm/ps. In the graph, a mark o represents a measurement result when the FiO$_2$ concentration is 100%; Δ, 20%; and □, 15%. As shown in this graph, in the short wavelength range, the lower the FiO$_2$ concentration becomes, and the smaller the amount of oxygen supplied to the rat 64 becomes, the shorter the average optical pathlength becomes. A short average optical pathlength indicates a high light absorption in the head portion of the rat 64. This coincides with the Hb and HbO$_2$ light absorption profiles shown in the graph of FIG. 1. That is, in the graph of FIG. 14, the incident pulse light is greatly absorbed by the deoxygenated hemoglobin Hb in the short wavelength range, thus exhibiting the Hb spectra as shown in FIG. 1.

A substitution of the measurement result of this average optical pathlength into equation (18) yields the ratio of HbO$_2$ concentration to the Hb concentration. The resultant concentration ratio is substituted into equation (19) to calculate the degree (SO$_2$) of saturation of oxygen in the blood in the head portion of the rat. Table 2 shows the SO$_2$ value obtained from each measurement result represented by each black plot in the graph shown in FIG. 14. These plots represent the measurement results with respect to the incident pulse light components having the wavelengths of 740, 755, and 800 nm.

TABLE 2

| Plot | FiO$_2$ [%] | Average Optical PathLength C<t> [nm] | | | SO$_2$ value |
|---|---|---|---|---|---|
| | | 740 | 755 | 800 | |
| o | 100 | 9.1 | 8.7 | 8.8 | 75 |
| Δ | 20 | 8.6 | 8.1 | 8.7 | 54 |
| □ | 15 | 8.5 | 8.0 | 9.1 | 39 |

As can be understood from the above table, the calculated SO$_2$ value reflects the inhalation oxygen concentration (FiO$_2$). When the concentration FiO$_2$ decreases, the SO$_2$ value also decreases.

The same effect as in each previous embodiment can be obtained in the third embodiment. The degree of saturation of oxygen in the blood of the living tissue can be easily and accurately measured with a simple apparatus arrangement.

What is claimed is:

1. A method of measuring a concentration of an absorptive constituent in a scattering medium, comprising the steps of:

(a) causing light having a wavelength to be incident on a scattering medium at a first position, said scattering medium containing two types of absorptive constituents, A and B;

(b) detecting light scattered by said scattering medium at a second position;

(c) calculating at least one of an average optical pathlength and a mean flight time of the light in the scattering medium;

(d) changing the wavelength of the light and repeating step (a), step (b) and step (c) n+1 times;

(e) obtaining a difference between values calculated in step (c), wherein said difference is at least one of an average optical pathlength difference and a mean flight time difference of light of different wavelengths in the scattering medium;

(f) obtaining a concentration ratio of respective absorptive constituents in said scattering medium in accordance with a relationship representing that one of the average optical pathlength difference and the mean flight time difference is inversely proportional to a difference in absorbance of the absorptive constituents for light of different wavelengths;

wherein the light incident on said scattering medium has three different wavelengths λ1, λ2, and λ3; and wherein a ratio $V_A : V_B$ of a concentration $V_A$ to a concentration $V_B$ of said absorptive constituents A and B in said scattering medium is determined according to the following equation:

$$V_A : V_B = \{(\epsilon_{B\lambda3} - \epsilon_{B\lambda1})\Delta\!<\!t\!>_{\lambda2,\lambda1} - (\epsilon_{B\lambda2} - \epsilon_{B\lambda1})\Delta\!<\!t\!>_{\lambda3,\lambda1}\} : \{-(\epsilon_{A\lambda3} - \epsilon_{A\lambda1})\Delta\!<\!t\!>_{\lambda2,\lambda1} + (\epsilon_{A\lambda2} - \epsilon_{A\lambda1})\Delta\!<\!t\!>_{\lambda3,\lambda1}\}$$

where $\Delta\!<\!t\!>_{\lambda2,\lambda1}$ is the mean flight time difference between the light incident on said scattering medium having wavelengths λ2 and λ1;

$\Delta\!<\!t\!>_{\lambda3,\lambda1}$ is a mean flight time difference between the incident light having wavelengths λ3 and λ1;

$\epsilon_{A\lambda1}$ and $\epsilon_{B\lambda1}$ are extinction coefficients of said absorptive constituents A and B with respect to the incident light having the wavelength λ1;

$\epsilon_{A\lambda2}$ and $\epsilon_{B\lambda2}$ are extinction coefficients of said absorptive constituents A and B with respect to the incident light having the wavelength λ2; and $\epsilon_{A\lambda3}$ and $\epsilon_{B\lambda3}$ are extinction coefficients of said absorptive constituents A and B with respect to the incident light having the wavelength λ3.

2. The method according to claim 1, wherein said step of calculating at least one of an average optical pathlength, comprises the steps of:

causing pulsed light to be incident on said scattering medium, detecting each photon reaching the second position with different delay times upon incidence of each light pulse;

dividing a sum of the delay times of the photons detected by a number of photons detected to obtain a quotient; and multiplying the quotient by the speed of light in the scattering medium.

3. The method of according to claim 1, wherein said scattering medium is a living tissue, said absorptive constituents are deoxygenated hemoglobin Hb and oxyhemoglobin HbO$_2$ in blood in the living tissue, the light incident on said scattering medium has a wavelength range of from 600 nm to 1.5 μm, and a degree of saturation of oxygen in the blood in the living tissue is obtained on the basis of the determined ratio of the absorptive constituent concentrations.

4. The method of measuring according to claim 1, wherein said step of detecting comprises the step of detecting each photon reaching said second position with different delay times upon incidence of each light pulse, and said step of calculating comprises the step of:

calculating the optical pathlength C<t> using a following formula:

where N is the number of measured photons, $$C\langle t\rangle = \frac{C\sum_{n}^{N} T_n}{N}$$

C is a speed of light in the scattering medium, $T_n$ is a delay time of the $n_{th}$ photon.

5. A method of measuring a concentration of an absorptive constituent in a scattering medium according to claim 1, wherein said light incident on the scattering medium is in the form of light pulses, and wherein the average optical pathlength is calculated by the steps of:

detecting a light intensity of each light pulse obtained in the detecting step with a predetermined delay time after each light pulse is incident on said scattering medium;

calculating the optical pathlength C<t> using a following formula:

$$C\langle t\rangle = \frac{C\sum_{n} t_n f(t_n)}{\sum_{n} f(t_n)}$$

where $t_n$ (=$t_1, t_2, t_3, \ldots$) is a $n_{th}$ delay time, $f_n$ is a light intensity corresponding to $t_n$, and C is a speed of light in the scattering medium.

6. An apparatus for measuring a concentration of an absorptive constituent in a scattering medium, comprising:

a light source for generating light pulses;

wavelength control means for controlling a wavelength of each said light pulse;

light guide means for causing the light from said light source to be incident on a scattering medium at a first position, said scattering medium containing two types of absorptive constituents, A and B;

photodetecting means for receiving, at a second position, light pulses scattered within said scattering medium, and time-resolved measuring each received light pulse;

one of optical pathlength calculating means and flight time calculating means for calculating one of n+1 average optical pathlengths and n+1 mean flight times of respective n+1 light pulses having n+1 wavelengths in accordance with time-resolved measurement results of said photodetecting means;

concentration calculating means for obtaining one of an average optical pathlength difference and a mean flight time difference between light pulses having two wavelengths from one of the average optical pathlengths and the mean flight times calculated by one of said optical pathlength calculating means and said flight time calculating means, and for obtaining a ratio of the absorptive constituent concentrations in said scattering medium in accordance with a relationship representing that one of the average optical pathlength difference and the mean flight time difference is inversely proportional to a difference in absorbance of the absorptive constituent for light of two wavelengths;

wherein said light source emits light pulses having three different wavelengths $\lambda 1$, $\lambda 2$, and $\lambda 3$; and wherein said concentration calculating means calculates a ratio $V_A : V_B$ of a concentration $V_A$ to a concentration $V_B$ of said absorptive constituents A and B in said scattering medium according to the following formula:

$$V_A : V_B = \{(\epsilon_{B\lambda 3} - \epsilon_{B\lambda 1})\Delta\langle t\rangle_{\lambda 2,\lambda 1} - (\epsilon_{B\lambda 2} - \epsilon_{B\lambda 1})\Delta\langle t\rangle_{\lambda 3,\lambda 1}\} : \{-(\epsilon_{A\lambda 3} - \epsilon_{A\lambda 1})\Delta\langle t\rangle_{\lambda 2,\lambda 1} + (\epsilon_{A\lambda 2} - \epsilon_{A\lambda 1})\Delta\langle t\rangle_{\lambda 3,\lambda 1}\}$$

where $\Delta\langle t\rangle_{\lambda 2,\lambda 1}$ is a mean flight time difference between incident light pulses having wavelengths $\lambda 2$ and $\lambda 1$;

$\Delta\langle t\rangle_{\lambda 3,\lambda 1}$ is a mean flight time difference between incident light pulses having wavelengths $\lambda 3$ and $\lambda 1$;

$\epsilon_{B\lambda 1}$ are extinction coefficients of said absorptive constituents A and B with respect to the incident light pulses having the wavelength $\lambda 1$;

$\epsilon_{A\lambda 2}$ and $\epsilon_{B\lambda 2}$ are extinction coefficients of said absorptive constituents A and B with respect to the incident light pulses having the wavelength $\lambda 2$; and $\epsilon_{A\lambda 3}$ and $\epsilon_{B\lambda 3}$ are extinction coefficients of said absorptive constituents A and B with respect to the incident light pulses having the wavelength $\lambda 3$.

7. An apparatus according to claim 6, wherein said light source emits pulsed light having a wavelength between 600 nm and 1.5 µm, said scattering medium is a living tissue, said absorptive constituents are deoxygenated hemoglobin Hb and oxyhemoglobin $HbO_2$ in blood in the living tissue, and said apparatus further comprises $SO_2$ value calculating means for obtaining a degree of saturation of oxygen in the blood of the living tissue on the basis of the ratio of said absorptive constituent concentrations output from said concentration calculating means.

\* \* \* \* \*